United States Patent [19]

Zeh

[11] Patent Number: 5,038,623
[45] Date of Patent: Aug. 13, 1991

[54] DEVICE FOR TAKING SAMPLES OF RADIOACTIVE AND/OR TOXIC SUSPENSIONS CONTAINING SOLIDS

[75] Inventor: Horst Zeh, Karlsruhe, Fed. Rep. of Germany

[73] Assignee: Deutsche Gesellschaft fur Wiederaufarbeitung von Kernbrennstoffen mbH, Hanover, Fed. Rep. of Germany

[21] Appl. No.: 497,316

[22] Filed: Mar. 22, 1990

[30] Foreign Application Priority Data

Mar. 22, 1989 [DE] Fed. Rep. of Germany ....... 3909438

[51] Int. Cl.$^5$ .............................................. G01N 1/14
[52] U.S. Cl. ............................... 73/863.83; 73/864.74
[58] Field of Search ......... 73/863.41, 863.43, 863.51, 73/863.58, 863.61, 863.71, 864.34, 864.73, 864.74, 863.83, 863.84, 864.35; 285/95

[56] References Cited

U.S. PATENT DOCUMENTS

| 2,759,743 | 8/1956 | Bloom | 285/95 |
| 4,494,413 | 1/1985 | Bukkems et al. | 73/863.43 |
| 4,635,969 | 1/1987 | Jackson | 285/95 |
| 4,638,675 | 1/1987 | Sperinck et al. | 73/864.73 |
| 4,653,333 | 3/1987 | Zeh | 863.81/73 |

FOREIGN PATENT DOCUMENTS 3044424 6/1982 Fed. Rep. of Germany .

Primary Examiner—Robert Raevis
Attorney, Agent, or Firm—Walter Ottesen

[57] ABSTRACT

A device for taking samples of radioactive and/or toxic suspensions containing solids includes a single needle head for taking samples from a liquid circulating in a pipe loop. The liquid is drawn off into a sample vessel with the liquid being pumped by a vacuum-assisted air lift. In order to minimize the risk of clogging in such a sampling device and to be able to obtain reliably representative samples, the one-needle head has a mixing chamber which widens conically toward the interior of the housing of the sampling device. The feed line extends into this conical mixing chamber to a location just ahead of the needle opening in the base. The opening at the end of the feed line has a larger diameter than the inside diameter of the sampling needle disposed in the needle head. With this configuration, a higher flow velocity is achieved together with a high degree of turbulence of the liquid in the sampling device.

6 Claims, 2 Drawing Sheets

DEVICE FOR TAKING SAMPLES OF RADIOACTIVE AND/OR TOXIC SUSPENSIONS CONTAINING SOLIDS

FIELD OF THE INVENTION

The invention relates to a device for taking samples of radioactive and/or toxic suspensions containing solids. The device includes a single needle head for taking samples from a liquid circulating in a pipe loop.

BACKGROUND OF THE INVENTION

The known sampling devices in facilities for processing irradiated nuclear fuels use a combination of closed sample vessel and hollow needle filling to transfer the test solution into specimen flasks. The filling aperture of the sample vessel is in this case closed by a rubber septum which can be pierced by one or two hollow needles ground to an acute angle. Through these inserted hollow needles, the sample vessels are filled from a diverted component quantity of the pumped sample fluid.

U.S. Pat. No. 4,653,333 discloses a sampling device for radioactive and/or toxic substances. With this device, a sample vessel is filled by means of a pipe system through a single needle head within a shielded space. The hollow needle of the needle head is fixed in the axis of a rotary body having an end face facing toward the interior of the housing. This end face has a conical recess which tapers down to the needle diameter. At the end of the rotary body there is a feed chamber in the housing of the sampling device and the feed chamber is connected to a feed line. A return line is connected to the lowest point of the feed chamber.

The needle head has only one hollow needle which centrally pierces the septum which seals the sample vessel and is thereby centrally guided in the septum. Thus, it is possible to insert a larger needle which has the advantage of a reduced tendency to clog and which is less readily bent.

The results obtained with this known sampling device were satisfactory. Further improvements are, however, sought for use with suspensions containing solids and in order to obtain as far as possible representative specimens.

SUMMARY OF THE INVENTION

It is an object of the invention to provide a sampling device wherein the risk of clogging is further minimized and with which a sample as representative as possible can be reliably obtained.

The sampling device of the invention is for taking a sample of a radioactive and/or toxic suspension containing solids from a liquid circulating in a pipe loop. The pipe loop includes a feed line for conducting the liquid to the sampling device and a return line for conducting the liquid away therefrom. The liquid in the pipe loop is pumped via a vacuum-supported air lift. The sampling device includes: a housing having an opening formed therein to define the interior thereof; a needle head seated in the opening; the needle head having a cavity formed therein to define a mixing chamber, the mixing chamber having a base and expanding from the base with a conical taper into the interior; a sampling needle for conducting a portion of the liquid away from the chamber, the needle having a needle opening and being mounted in the needle head so as to cause the needle opening to communicate with the chamber, the needle opening having an inner diameter; the feed line having an end portion extending into the mixing chamber and the end portion having a feed opening in spaced relationship to the base and in front of the needle opening; the feed opening having a diameter greater than the inner diameter of the needle opening; the mixing chamber having an outer end spaced from the base; and, return means formed in the outer end for conducting the liquid into the return line.

Air lift pumping imparts a pulsation to the fluid being pumped. Via the submerged air lift connection, slugs of air are introduced into the column of liquid which is raised in the feed line by negative pressure. The pressure which builds up pushes the column of liquid upwards in a pulsating manner. The column of liquid becomes lighter because of the bubbles introduced. The pulsating pumping causes turbulence in the solids and results in rapid filling by injection as well as partial rinsing of the liquid out of the sample vessel during a pause in pulsation.

By means of the arrangement of the feed line close to the base of the mixing chamber, a pressure build-up is achieved in the mixing chamber to produce swirling of the solids. The differing dimensions result in variations in flow velocity which produce a pressure head. The result is substantial turbulence in the needle head housing and thus an advantageous turbulence of the solids and a homogenization of the suspension, whereby the danger of clogging is also minimized. The narrow spaces in the needle head are advantageous for turbulence.

The cone-shaped configuration of the mixing chamber of the needle head is ideal for emptying when the negative pressure in the sampling loop is raised. The housing of the sampling device is, as is conventional in the sampling system, mounted at the uppermost location of the pipe loop so that the housing empties when there is an interruption in the negative pressure.

According to another embodiment of the invention, the feed line ends in the mixing chamber in a nozzle extension which is conically tapered with the inclination of the outer surface of the nozzle extension corresponding to the inclination of the conically expanded mixing chamber. If the feed line ends in a nozzle ahead of the base of the mixing chamber, then a high propagation of pressure is achieved which extends into the sample vessel. Because of the configuration of the nozzle, increased velocity is imparted to the incoming medium which helps to raise the pressure in the vessel thereby ensuring the return flow from the vessel.

A pulsating pressure is generated in the sample vessel through the feed line which ends as a nozzle in the needle head housing and the pressure peak of the pulsating pressure is greater than the maximum pressure in the needle head housing. Thus, relatively large quantities of sample are involved in flushing the vessel and they increase the sample exchange rate. This embodiment is suitable for sampling systems in which the sample vessel is fitted onto the needle before the pump loop is switched on and where it is necessary to flush out the system feed which is to be rejected.

In an advantageous embodiment of the invention, the nozzle opening is 1.5 to 1.8 times larger than the inside diameter of the sampling needle. It was determined that with this range of dimensions, a sufficient pulsating pressure is generated in the vessel. The exchange of the fluid sample in the sample vessel to obtain a sample as representative as possible is also achieved with a single needle.

According to another embodiment of the invention, the conical annular clear space between the feed nozzle and the inner wall of the needle head has a width of 2.5 to 3.5 mm. This narrow space supports the advantageous turbulence in the circulating fluid.

According to still another embodiment of the invention, the outer surface of the needle head has a cone-like configuration. This causes the needle head to self-tighten because of the negative pressure in the sampling system. Accordingly, it is possible to omit mechanical fixing means. The application of this conical fit has considerable advantages for the remotely manipulated exchange of a needle head.

The invention makes it possible to draw off representative samples of solids-containing liquids without any risk of clogging. In accordance with the invention, this is achieved essentially by the combination of the pulsating pumping in conjunction with the pressure-building embodiments of the sampling device of the invention.

BRIEF DESCRIPTION OF THE DRAWINGS

The invention will now be explained with reference to the drawings, wherein.

DESCRIPTION OF THE PREFERRED EMBODIMENTS OF THE INVENTION

Figure 1:
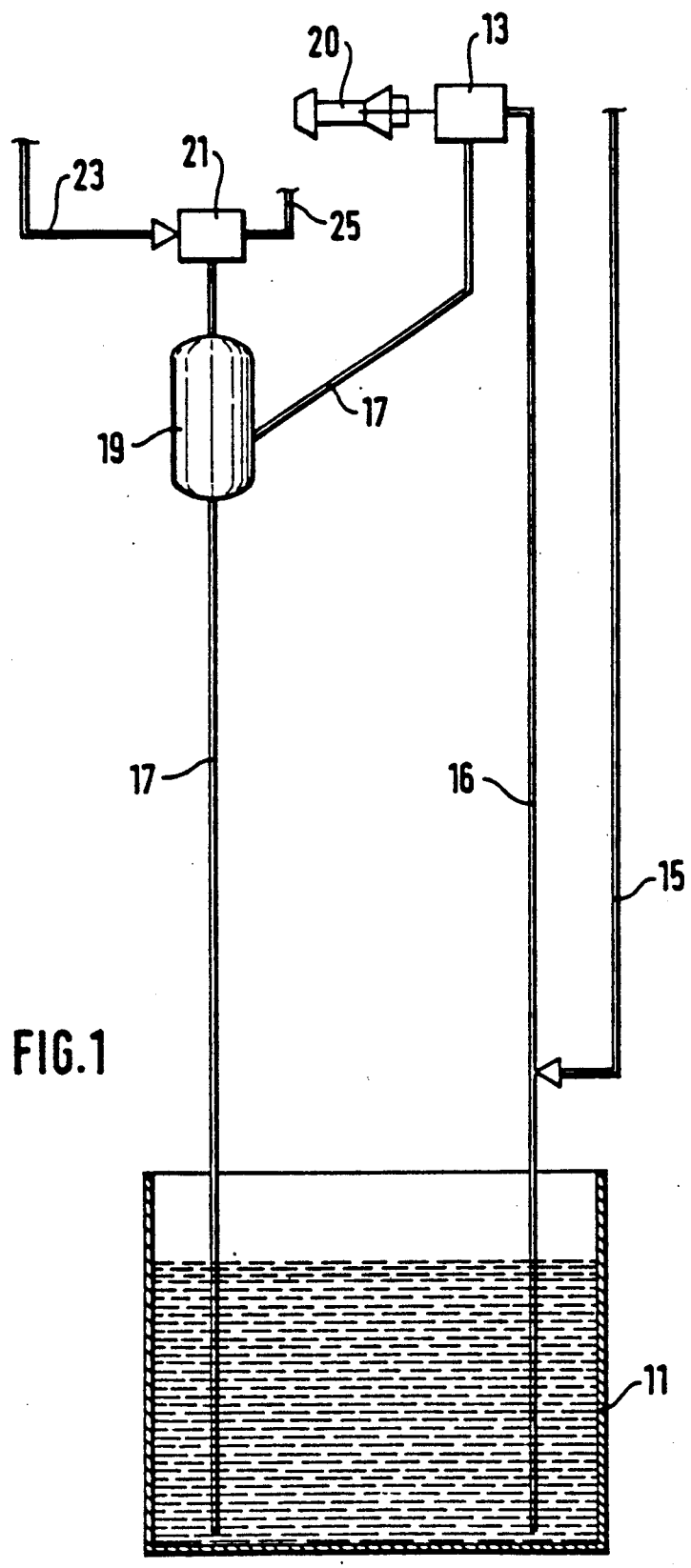
FIG. 1 is a schematic of a sampling loop with the sampling device according to the invention being disposed at the highest position in the loop.

FIG. 1 is a schematic of a sampling loop for a radioactive suspension containing solids with the suspension being in a process vessel 11. The flow of liquid is pumped from this process vessel 11 to a sampling device 13 disposed at the uppermost location of the loop by means of a vacuum-assisted air lift system 15 which provides the pumping force for circulation. For this purpose, the process vessel 11 is provided with an feed line 16 having an end portion immersed in the liquid and which extends up to the sampling device 13. A return line 17 from the sampling device 13 leads to a venting vessel 19. From there, the return line 17 extends farther to the process vessel 11 where the lower end portion of this line is likewise immersed in the liquid.

A sample vessel 20 can be fitted to the sampling device 13.

In a manner known per se, the process flow is pumped, by an air lift device 15 by which compressed air is introduced into the feed line 16 in the form of slugs of air. The venting vessel 19 is connected into the return line 17 and is connected to an ejector 21 to generate a negative pressure. The ejector 21 is supplied with compressed air by a compressed air line 23 and has a venting line 25.

Figure 2:
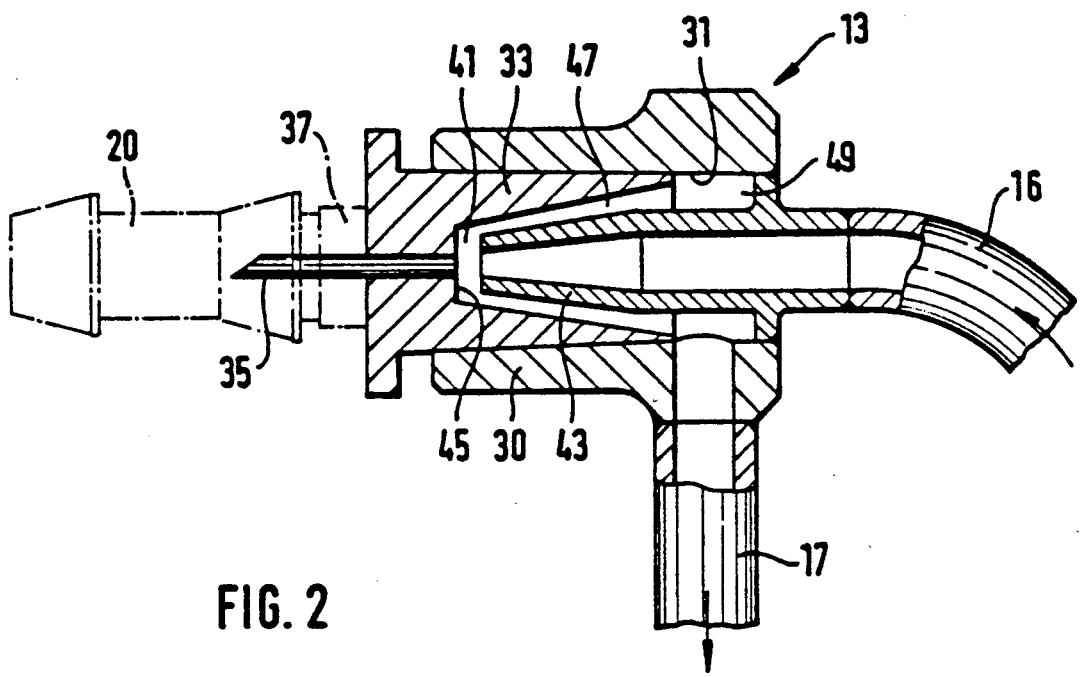
FIG. 2 shows a sampling device of the invention, in section, with a needle head inserted in the housing of the sampling device; and, FIG. 3 shows a modified embodiment of the sampling device according to the invention.

The sampling device 13 shown in FIG. 2 has a housing 30 which, in turn, has a conically widening housing bore 31 formed therein. A needle head 33 in the form of a truncated cone is inserted into the bore 31. The needle head 33 has a hollow sampling needle 35 mounted on its central axis. This needle pierces a septum 37 on the sample vessel 20 when the sampling device 13 is in use. The needle head 33 has a cavity bored out to form a mixing chamber 41. The mixing chamber 41 opens toward the interior of the housing 30 and widens conically toward the latter.

The feed line 16 extends along the axis of the needle head 33 and has a nozzle extension 43 with which it projects into the conical mixing chamber 41 of the needle head 33 to a point just before the base 45 of the mixing chamber 41. An annular space 47 is provided between the feed nozzle 43 and the mixing chamber 41. At the end of the needle head 33, this annular space 47 communicates with the return line 17 via an annular housing space 49. The return line 17 is connected to the housing 30 at the lowest point of the housing space 49.

The sampling device operates in the manner described below.

Before the pumping loop is switched on, the sample vessel is fitted onto the needle of the sampling device. The ejector 21 is activated and develops a negative pressure in the filling system by which a column of liquid in the feed line 16 is raised. The connection of the air lift 15 leads directly into this column of liquid. The sample medium is pumped by applying compressed air through the air lift line 15.

The sample vessel is perforce filled with a component quantity of the liquid present in the feed line 16. This feed cannot be used as a representative sampling. Once the loop has been switched on, it is maintained in operation for a while and the sample vessel is continuously flushed by a component quantity of the circulating liquid. After a predetermined time, fixed according to flow velocity of the medium, a representative sample of homogenized liquid is present in the sample vessel.

Because of the nozzle shape 43 of the segment of the feed line 16 which ends in the mixing chamber 41 of the needle head 33, a pulsating negative pressure is developed which extends into the sample vessel 20. The pressure peaks are above the pressures in the needle head housing. Thus, larger quantities of samples are involved in flushing the sample vessel and enhance the exchange rate of the sample. Therefore, liquid can be forced back during the pauses in pulsation.

After the predetermined flushing time, the air lift pump is shut down and the introduction of air ceases. The sample vessel 20 is removed from the sampling device 13. Immediately thereafter, the negative pressure in the pumping loop is switched off. This sequence of steps affords the advantage of preventing dripping from the hollow sampling needle 35. The sampling needle 35 is flushed clear into the pumping loop by the brief action of the negative pressure when the sample vessel 20 is removed.

Figure 3:
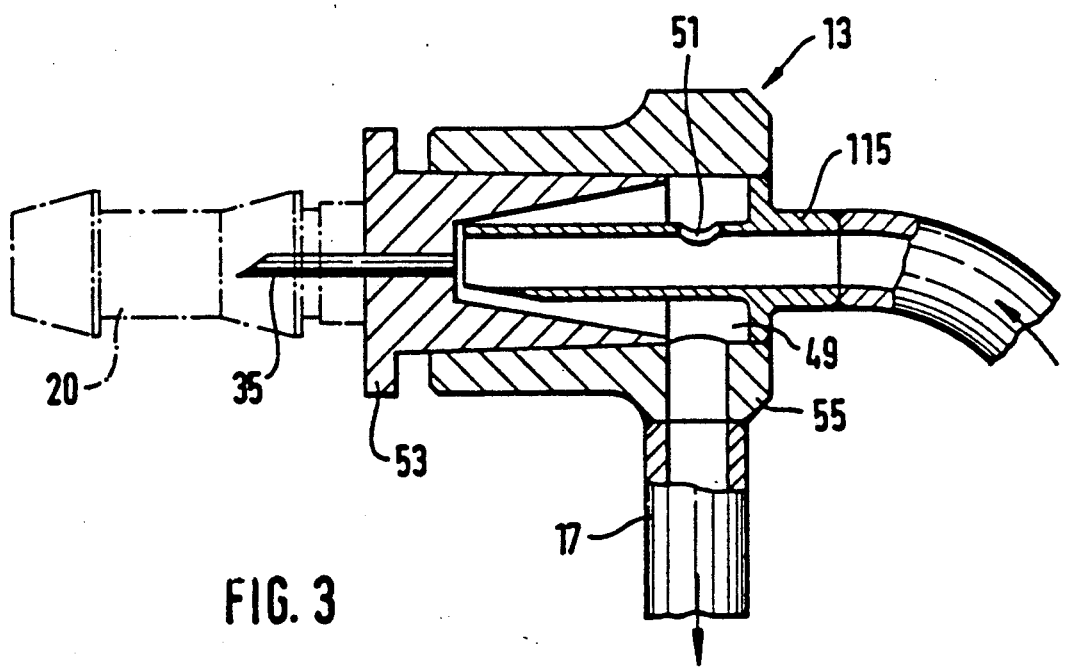

The modified embodiment (FIG. 3) of sampling device 13 makes it possible for the feed fluid to be pumped without the sample vessel 20 already being mounted on the needle 35. In order to prevent leakage from the open needle 35 during this phase of the operation, the feed line 15 in the needle head 33 has no taper. Furthermore, in order to suppress pressure peaks, the feed line additionally communicates with an upper venting port 51 in the annular space 49 to which the return line 17 is connected.

The flange 53 provided at the outer end of the needle head 33 is used for manipulating the needle head 33 when this is exchanged and removed from the housing 55 of the stationary sampling device 13.

With this embodiment, a sample can be taken more rapidly. The feed liquid is already pumped without a sample vessel being mounted on the needle 35. In order to prevent leakage from the open needle 35 during this phase of operation, the feed line 16 ends in the mixing chamber 41 of the needle head 33 without a narrowing taper and, in order to suppress pressure peaks, the feed line 16 has a venting port 51 at the elevation of the annular space 49. The sample vessel 20 is filled and can be removed again immediately after filling is completed.

It is understood that the foregoing description is that of the preferred embodiments of the invention and that various changes and modifications may be made thereto without departing from the spirit and scope of the invention as defined in the appended claims.

What is claimed is:

1. A sampling device for taking a sample of a radioactive and/or toxic suspension containing solids from a liquid circulating in a pipe loop including a feed line for conducting the liquid to the sampling device and a return line for conducting the liquid away therefrom and wherein the liquid is pumped via a vacuum-supported air lift, the sampling device comprising:

a housing having an opening formed therein to define the interior thereof;

a needle head seated in said opening;

said needle head having a cavity formed therein to define a mixing chamber, said mixing chamber having a substantially flat base and expanding from said flat base with a conically tapered surface into said interior so as to cause said mixing chamber to have a shape corresponding to a truncated cone;

a sampling needle for conducting a portion of the liquid away from said chamber, said needle having a needle opening and being mounted in said needle head so as to cause said needle opening to communicate with said chamber, said needle opening having an inner diameter;

said feed line having an end portion extending into said mixing chamber and said end portion having a feed opening in spaced relationship to said flat base and in front of said needle opening;

said end portion extending deeply into said mixing chamber to just ahead of said base so as to cause said base to define a baffle face for receiving the liquid from said feed opening thereagainst to produce a swirling of the solids contained in the liquid; and, return means formed in said housing so as to communicate with said mixing chamber for conducting the liquid from said chamber into the return line.

2. The sampling device of claim 1, said feed opening having a diameter greater than said inner diameter of said needle opening; and, said end portion of said feed line defining a conically tapered nozzle extension having a conically tapered outer surface having an inclination corresponding to the inclination of said conically tapered surface of said mixing chamber.

3. The sampling device of claim 2, said nozzle extension defining a nozzle opening having a diameter greater than said inner diameter of said sampling needle by a factor lying in the range of 1.5 to 1.8.

4. The sampling device of claim 2, said conically tapered surface of said mixing chamber and said outer surface of said nozzle extension conjointly defining an annular conical space having a clear width lying in the range of 2.5 to 3.5 mm.

5. The sampling device of claim 2, said opening in said housing being a conical bore and said needle head being configured to define a truncated conical member which can be seated in said conical bore.

6. The sampling device of claim 1, said feed opening having a diameter greater than said inner diameter of said needle opening; and, said feed line having an inner first diameter and said end portion defining a channel which tapers to said feed opening so as to cause said feed opening to have a second diameter less than said first diameter thereby defining a nozzle.

* * * * *